United States Patent
Silverman et al.

(10) Patent No.: US 7,364,591 B2
(45) Date of Patent: *Apr. 29, 2008

(54) METHOD FOR TREATING MORBID OBESITY

(75) Inventors: David E. Silverman, Fall City, WA (US); Alan Stein, Bellingham, WA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/435,462

(22) Filed: May 16, 2006

(65) Prior Publication Data

US 2006/0249165 A1    Nov. 9, 2006

Related U.S. Application Data

(63) Continuation of application No. 10/964,596, filed on Oct. 12, 2004, now Pat. No. 7,044,979, which is a continuation of application No. 10/386,241, filed on Mar. 10, 2003, now Pat. No. 6,802,868, which is a continuation of application No. 09/709,236, filed on Nov. 10, 2000, now Pat. No. 6,540,789.

(60) Provisional application No. 60/212,072, filed on Jun. 15, 2000.

(51) Int. Cl.
*A61F 2/00* (2006.01)
(52) U.S. Cl. .................. 623/23.65; 607/40; 600/29
(58) Field of Classification Search ............. 623/23.65, 623/23.68; 607/40; 600/29
See application file for complete search history.

(56) References Cited

U.S. PATENT DOCUMENTS

| | | | |
|---|---|---|---|
| 3,094,122 A | 6/1963 | Gauthier et al. |
| 3,204,634 A | 9/1965 | Koehn |
| 4,271,827 A | 6/1981 | Angelchik |
| 4,351,333 A | 9/1982 | Lazarus et al. |
| 4,424,208 A | 1/1984 | Wallace et al. |
| 4,582,640 A | 4/1986 | Smestad et al. |
| 4,592,339 A | 6/1986 | Kuzmak et al. |
| 4,773,393 A | 9/1988 | Haber et al. |
| 4,803,075 A | 2/1989 | Wallace et al. |
| 4,837,285 A | 6/1989 | Berg et al. |

(Continued)

FOREIGN PATENT DOCUMENTS

AU    A 34223/95    5/1996

(Continued)

OTHER PUBLICATIONS

P. Donahue et al., "Endoscopic Sclerosis Of The Gastric Cardia For Prevention Of Experimental Gastroesophageal Reflux", (1990) *Gastrointestinal Endoscopy*, pp. 253-258.

(Continued)

*Primary Examiner*—Suzette Gherbi
(74) *Attorney, Agent, or Firm*—Dorsey & Whitney LLP

(57) ABSTRACT

A method for treating morbid obesity in a body of a mammal having a gastrointestinal tract extending through a stomach and a pyloric sphincter and a wall forming the stomach and pyloric sphincter. At least one implant is formed in the wall in the vicinity of the pyloric sphincter to inhibit emptying of the stomach.

19 Claims, 7 Drawing Sheets

U.S. PATENT DOCUMENTS

| | | | |
|---|---|---|---|
| 5,007,940 A | 4/1991 | Berg | |
| 5,067,965 A | 11/1991 | Ersek et al. | |
| 5,074,868 A | 12/1991 | Kuzmak | |
| 5,116,387 A | 5/1992 | Berg | |
| 5,158,573 A | 10/1992 | Berg | |
| 5,204,382 A | 4/1993 | Wallace et al. | |
| 5,258,028 A | 11/1993 | Ersek et al. | |
| 5,301,682 A | 4/1994 | Debbas | |
| 5,314,473 A | 5/1994 | Godin | |
| 5,336,263 A | 8/1994 | Ersek et al. | |
| 5,423,872 A * | 6/1995 | Cigaina | 607/40 |
| 5,451,406 A | 9/1995 | Lawin et al. | |
| 5,480,644 A | 1/1996 | Freed | |
| 5,490,984 A | 2/1996 | Freed | |
| 5,580,568 A | 12/1996 | Greff et al. | |
| 5,667,767 A | 9/1997 | Greff et al. | |
| 5,695,480 A | 12/1997 | Evans et al. | |
| 5,702,361 A | 12/1997 | Evans et al. | |
| 5,755,658 A | 5/1998 | Wallace et al. | |
| 5,785,642 A | 7/1998 | Wallace et al. | |
| 5,792,478 A | 8/1998 | Lawin et al. | |
| 5,820,584 A | 10/1998 | Crabb | |
| 5,830,178 A | 11/1998 | Jones et al. | |
| 5,861,036 A | 1/1999 | Godin | |
| 5,919,233 A | 7/1999 | Knopf et al. | |
| 6,098,629 A * | 8/2000 | Johnson et al. | 128/897 |
| 6,251,064 B1 | 6/2001 | Silverman et al. | |
| 6,271,278 B1 | 8/2001 | Park et al. | |
| 6,358,197 B1 | 3/2002 | Silverman et al. | |
| 6,605,294 B2 | 8/2003 | Sawhney | |
| 6,605,518 B1 | 8/2003 | Ohmi et al. | |
| 6,615,084 B1 | 9/2003 | Cigaina | |
| 7,185,657 B1 * | 3/2007 | Johnson et al. | 128/898 |
| 2001/0046518 A1 | 11/2001 | Sawhney | |
| 2003/0040804 A1 | 2/2003 | Stack et al. | |
| 2003/0093157 A1 | 5/2003 | Casares et al. | |

FOREIGN PATENT DOCUMENTS

| | | |
|---|---|---|
| WO | WO 97/19643 | 6/1997 |
| WO | WO 97/45131 | 12/1997 |
| WO | WO 98/01088 | 1/1998 |
| WO | WO 98/17200 | 4/1998 |
| WO | WO 98/17201 | 4/1998 |

OTHER PUBLICATIONS

Society of Am. Gastrointestinal Endoscopic Surgeons, Los Angeles, CA, "Granting of Privileges for Laparascopic General Surgery", (Mar. 1991), Am. Jrnl. of Surgery, vol. 161, pp. 324-325.
Aye, R.W. et al., "Early Results With the Laparoscopic Hill Repair", (May 1994), Am. Jrnl. Of Surgery, vol. 167, pp. 542-546.
Caremax-Surgury for Obesity, www.caremax.org.
Collard, J.M. et al., "Laparoscopic Antireflux Surgery/What is Real Progress?", (1994), Annals of Surgery, vol. 220, No. 2, pp. 146-154.
DeMeester, T.R. et al., "Nissen Fundoplication for Gastroesophageal Reflux Disease", (1986), Annals of Surgery, vol. 204, No. 1, pp. 9-20.
Donahue, P.E. et al., "The Floppy Nissen Fundoplication/Effective Long-term Control of Pathologic Reflux", (Jun. 1985), Arch Surg, vol. 120, pp. 663-668.
Ellis, Jr., F.H., "The Nissen Fundoplication", (1992), Ann. Thorac. Surg., vol. 54, pp. 1231-1235.
Grande, L. et al., "Value of Nissen fundoplication in patients with gastro-oesophageal reflux judged by long-term sympton control", (1994), Brit. Jrnl. of Surgery, vol. 81, pp. 548-550.
Hill, L.D. et al., "Laparoscopic Hill Repair", (Jan. 1994), Contemporary Surgery, vol. 44, No. 1, pp. 13-20.
Hunter, J.G. et al., "A Physiologic Approach to Laparoscopic Fundoplication for Gastroesophageal Reflux Disease", (1996), Annals of Surgery, vol. 223, No. 6, pp. 673-687.
Ireland, A.C. et al., "Mechanisms underlying the antireflux action of fundoplication", (1993), Gut, vol. 34, pp. 303-308.
Johansson, J. et al., "Outcome 5 years after 360° fundoplication for gastro-oesophageal reflux disease", (Jan. 1993), Brit. Jnl. of Surgery, vol. 80, pp. 46-49.
Kauer, W.K.H. et al., "Mixed Reflux of Gastric and Duodenal Juices Is More Harmful to the Esophagus than Gastric Juice Alone/The Need for Surgical Therapy Re-Emphasized", (1995) Annals of Surgery, vol. 24, pp. No. 4, pp. 525-533.
Klingman, R.R. et al., "The Current Management of Gastroesophageal Reflux", (1991), Adv. Surg., vol. 24, pp. 259-291.
Little, A.G., "Mechanisms of Action of Antireflux Surgery: Theory and Fact", (1992), World Jnl. of Surgery, vol. 16, pp. 320-325.
Luostarinen, M., "Nissen Fundoplication for Reflux Esophagitis/Long-Term Clinical and Endoscopic Results in 109 of 127 Consecutive Patients", (1993), Annals of Surgery, vol. 217, No. 4, pp. 329-337.
Luostarinen, M. et al., "Fate of Nissen fundoplication after 20 years. A clinical, endoscopical, and functional analysis", (1993), Gut, vol. 34, pp. 1015-1020.
Malizia, A. et al., "Migration and Granulomatous Reaction After Periurethral injection of Polytef (Teflon)", (Jun. 1984), JAMA, vol. 251, No. 24, pp. 3277-3281.
Martin, C. et al., "Collis-Nissen Gastroplasty Fundoplasty Fundoplication For Complicated Gastro-Oesophageal Reflux Disease", (1992), Aust. N.Z. Jnl. Surg., vol. 62, pp. 126-129.
O'Connor, K.W. et al., "Endoscopic placement of collagen at the lower esophageal sphincter to inhibit gastroesophageal reflux: a pilot study of 10 medically intractable patients", (1998), Gastrointestinal Endoscopy, vol. 34, No. 2, pp. 106-112.
O'Connor, K. W. et al., "An experimental endoscopic technique for reversing gastroesophageal reflux in dogs by injecting inert material in the distal esophagus", (1984) Gatrointestinal Endoscopy, vol. 30, No. 5, pp. 275-280.
Ortiz, A. et al., "Conservative treatment versus antireflux surgery in Barrett's oesophagus: long-term results of a prospective study", (1996), Brit. Jnl. of Surg., vol. 83, 274-278.
Politano, V. et al., "Periurethral Teflon Injection for Urinary Incontinence", (Feb. 1974) Jnl. Urology, vol. 111, pp. 180-183.
Pope, C., "The Quality of Life Following Antireflux Surgery", (1992), World Jnl. of Surgery, vol. 16, pp. 355-358.
Schulman, C.C. et al, "Endoscopic injections of Teflon to treat urinary incontinence in women", (Jan. 21, 1984) BMJ, vol. 228, p. 192.
Shafik, A., "Intraesophageal Polytef injection for the treatment of reflux esophagitis", (1996), Surgical Endoscopy, pp. 329-331.
Shirazi, S.S. et al., "Long-term Follow-up for Treatment of Complicated Chronic Reflux Esophagitis", (May 1987), Arch Surg, vol. 122, 548-552.
Spechler, S.J. et al., "Comparison of Medical and Surgicl Therapy for Complicated Gastroesophageal Reflux Disease in Veterans", (Mar. 19, 1992), NE Jnl. of Med, vol. 326, No. 12, pp. 786-792.
Spechler, S.J. et al., "The Columnar-Lined Esophagus, Intestinal Metaplasia, and Norman Barrett", (1996), Gastroenterology, vol. 110, pp. 614-621.
Thor, K.B. et al., "A Long-Term Randomized Prospective Trial of the Nissen Procedure Versus a Modified Toupet Technique", (Dec. 1989), Ann. Surg., vol. 210, No. 6, pp. 719-724.
Vaezi, M.F. et al., "Synergism of acid and duodenogastroesophageal reflux in complicated Barrett's esophagus", (1995), Surgery, vol. 117, pp. 699-704.
Walker, R.D. et al., "Injectable Bioglass as a Potential Substitute for Injectable Polytetrafluoroethylene", (Aug. 1992), J. Urol., vol. 148, pp. 645-647.
Waring, J.P. et al., "The Preoperative Evaluation of Patients Considered for Laparoscopic Antireflux Surgery", (1995), Am. Jnl. Of Gastroenterology, vol. 90, No. 1, pp. 35-38.

* cited by examiner

METHOD FOR TREATING MORBID OBESITY

The application is a continuation application of U.S. utility patent application Ser. No. 10/964,596 filed Oct. 12, 2004, now U.S. Pat. No. 7,044,979, which is a continuation of U.S. utility patent application Ser. No. 10/386,241 filed Mar. 10, 2003, now U.S. Pat. No. 6,802,868, which is a continuation application of U.S. utility patent application Ser. No. 09/709,236 filed Nov. 10, 2000, now U.S. Pat. No. 6,540,789, and claims priority to U.S. provisional patent application Ser. No. 60/212,072 filed Jun. 15, 2000, the entire contents of which are incorporated herein by this reference.

This invention pertains to the treatment of morbid obesity.

Numerous modalities are purported to treat morbid obesity. These include patient-specific dietary restrictions and nutritional supplementation, abdominoplasty or panniculectomy, gastric banding and/or stapling and the more invasive and surgically aggressive gastric bypass. There is a need for a method which is less invasive and more clinically efficacious in treating morbid obesity.

In general, it is an object of the present invention to provide a method for creating implants in natural body cavities accessible by natural body openings and more preferably in gastrointestinal tract passageways in order to treat morbid obesity.

Another object of the invention is to provide a method of the above character for enhancing the pylorus.

Another object of the invention is to provide a method of the above character for limiting distensibility of the stomach and prolonging satiety.

Another object of the invention is to provide a method of the above character which is safe and relatively non-invasive.

Additional objects and features of the invention will appear from the following description from which the preferred embodiments are set forth in detail in conjunction with the accompanying drawings.

In general, a method for treating morbid obesity in a body of a mammal having a gastrointestinal tract extending through a stomach and a pyloric sphincter formed by a wall is provided. At least one implant is formed in the wall in the vicinity of the pyloric sphincter to inhibit emptying of the stomach.

Figure 1:
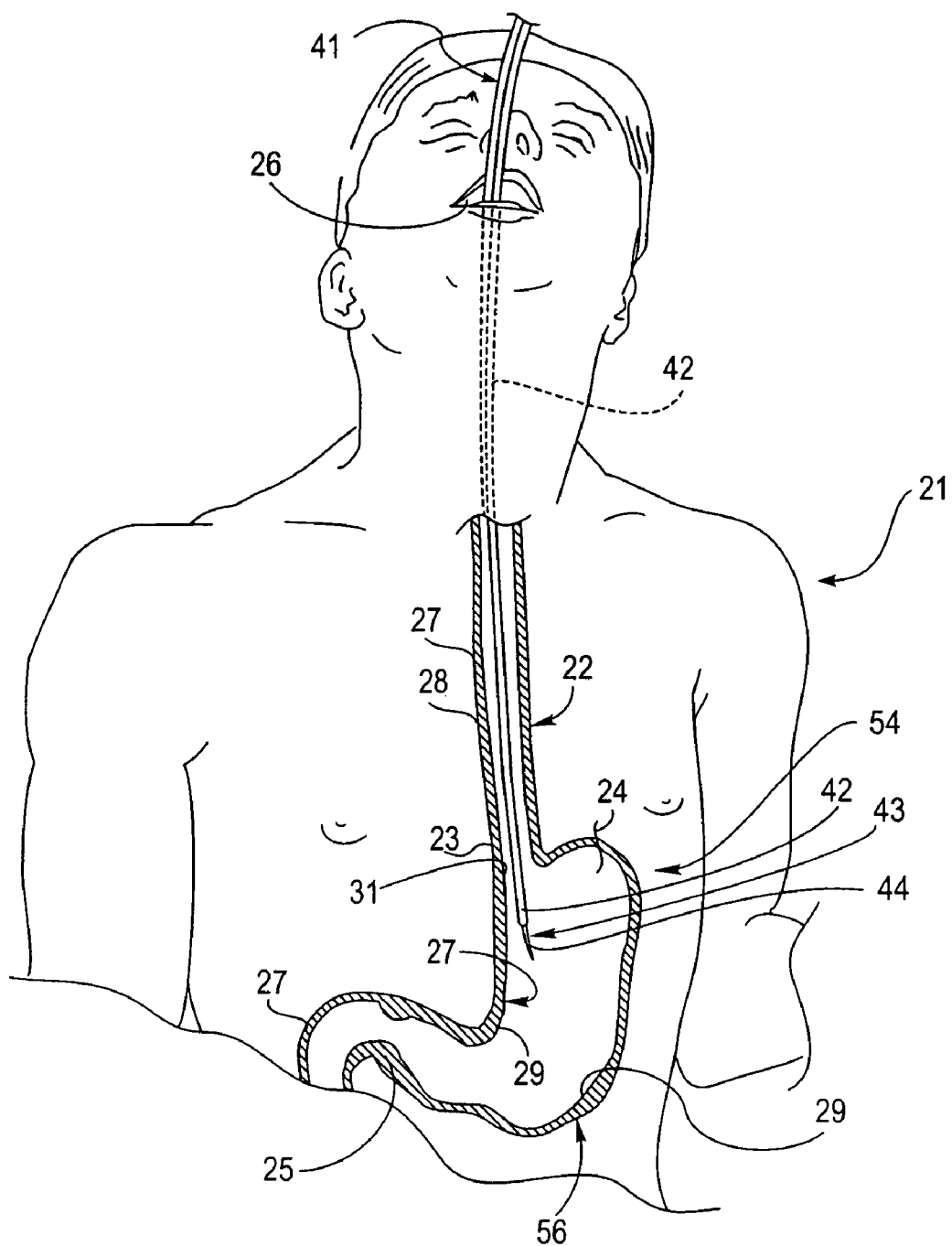
FIG. 1 is a schematic view with a device in place in the esophagus and stomach for performing the method of the present invention.

The method of the present invention is for use in a natural body cavity such as the gastrointestinal tract in a body of a mammal. A portion of a human body 21 is shown in FIG. 1 and has an internal cavity in the form of the passage of the esophagus 22 extending through a lower esophageal sphincter 23 to a stomach 24 and a pyloric sphincter 25. Such cavity is accessible by a natural body opening in the form of mouth 26 and is defined by wall 27. Esophagus 22, stomach 24 and pyloric sphincter 25 form part of the gastrointestinal tract of body 21 that extends from mouth 26 to an anus (not shown). The pylorus 25 is a one-way sphincter that serves as the anatomical junction between stomach 24 and the duodenum.

Esophageal mucosa 28 serves as the inner layer of the intraluminal wall 27 in esophagus 22 and the gastric mucosa 29 serves as the inner layer of the intramural wall 27 in stomach 24 and pylorus 25. Esophageal mucosa 28 and gastric mucosa 29 meet at the squamous columnar junction (not shown). Wall 27 has a muscle layer comprising a layer of circular muscle 32 extending beneath mucosa layers 28 and 29 and a layer of longitudinal muscle 33 beneath circular muscle 32. Muscle layers 32 and 33 extend around esophagus 22, stomach 24 and pylorus 25. Wall 27 further includes a submucosal layer or submucosa 34 extending between mucosa 29 and muscle layers 32 and 33. A submucosal space, that is a potential space, can be created between submucosa 34 and circular muscle layer 32 by the separation of layer 28 or 29 from muscle layer 32. In addition, as with any muscle, wall 27 includes an intramuscular potential space, that is a space which can be created intramuscularly by distension and separation of muscle fibers within a single muscle. Wall 27 has a depth or thickness which includes at least mucosal layers 28 and 29, submucosal layer 34, circular muscle layer 32 and longitudinal muscle layer 33.

The method of the present invention can be performed with any of the apparatus disclosed U.S. Pat. No. 6,251,063 and U.S. Pat. No. 6,238,335, the entire contents of each of which are incorporated herein by this reference. In general, a suitable apparatus or medical device 41 includes a probe member or probe 42 having an optical viewing device (not shown). Only a portion of device 41 has been shown in FIG. 1. A conventional or other suitable gastroscope or endoscope can be used as or with probe 42. A needle assembly 43 is slidably carried by probe 42. Needle assembly 43 can be of any conventional type, such as a modified sclerotherapy needle similar to the Bard® Flexitip™ needle manufactured by C.R. Bard, Inc. of Billerica, Md., and includes a needle member or needle 44 and a protective sleeve (not shown). Device 41 further includes a supply assembly (not shown) mounted to the proximal end portion of needle assembly 43. The supply assembly is secured to the proximal extremity of needle assembly 43 and can include a conventional syringe for introducing a liquid or solution through needle 44. The supply assembly optionally includes second and third reservoirs in the form of second and third syringes. The second syringe is filled with dimethyl sulfoxide (DMSO) or any other suitable liquid. The third syringe is filled with a saline solution or any other suitable aqueous or physiological solution.

In the method of the present invention, at least one implant forming material is introduced into the wall 27 of the gastrointestinal tract to form at least one implant therein. Exemplary implant-forming materials include any suitable material from which an implant can be formed when a fluid, separately or in conjunction with another fluid, is introduced into the tissue of a body. Other suitable implantable materials include any material capable of being delivered through a needle, solutions, suspensions, slurries, biodegradable or nonbiodegradable materials and two part or other mixtures. Exemplary implantable materials include injectable bioglass as described in Walker et al., "Injectable Bioglass as a Potential Substitute for Injectable Polytetrafluorethylene Particles", J.Urol., 148:645-7, 1992, small particle species such as polytetrafluoroethylene (PTFE) particles in glycerine such as Polytef®, biocompatible compositions comprising discrete, polymeric and silicone rubber bodies such as described in U.S. Pat. Nos. 5,007,940, 5,158,573 and 5,116,387 to Berg, biocompatible compositions comprising carbon coated beads such as disclosed in U.S. Pat. No. 5,451,406 to Lawin, collagen and other biodegradable material of the type disclosed in U.S. Pat. No. 4,803,075 to Wallace et al. and other known injectable materials.

Although aqueous or nonaqueous solutions are amongst the fluids that can be used, an inert, nonresorbable material is preferred. Preferred nonaqueous solutions are any of the solutions disclosed in International Application No. PCT/US99/29427 filed Dec. 10, 1999, the entire content of which is incorporated herein by this reference. One such material comprises at least one solution which when introduced into the body forms a nonbiodegradable solid. As used herein, a solid means any substance that does not flow perceptibly under moderate stress, has a definite capacity for resisting forces which tend to deform it (such as compression, tension and strain) and under ordinary conditions retains a definite size and shape; such a solid includes, without limitation, spongy and/or porous substances. One such embodiment of the at least one solution is first and second solutions which when combined in the body form the nonbiodegradable solid. Another such embodiment is a nonaqueous solution which can be introduced into the body as a liquid and from which a solid thereafter precipitates. A preferred embodiment of such a nonaqueous solution is a solution of a biocompatible polymer and a biompatible solvent which can optionally include a contrast agent for facilitating visualization of the solution in the body.

A particularly preferred implant forming solution is a composition comprising from about 2.5 to about 8.0 weight percent of a biocompatible polymer, from about 52 to about 87.5 weight percent of a biocompatible solvent and optionally from about 10 to about 40 weight percent of a biocompatible contrast agent having a preferred average particle size of about 10 μm or less. It should be appreciated that any percents stated herein which include a contrast agent would be proportionally adjusted when the contrast agent is not utilized. Any contrast agent is preferably a water insoluble biocompatible contrast agent. The weight percent of the polymer, contrast agent and biocompatible solvent is based on the total weight of the complete composition. In a preferred embodiment, the water insoluble, biocompatible contrast agent is selected from the group consisting of barium sulfate, tantalum powder and tantalum oxide. In still a further preferred embodiment, the biocompatible solvent is dimethylsulfoxide (DMSO), ethanol, ethyl lactate or acetone.

The term "biocompatible polymer" refers to polymers which, in the amounts employed, are non-toxic, chemically inert, and substantially non-immunogenic when used internally in the patient and which are substantially insoluble in physiologic liquids. Suitable biocompatible polymers include, by way of example, cellulose acetates (including cellulose diacetate), ethylene vinyl alcohol copolymers, hydrogels (e.g., acrylics), poly($C_1$-$C_6$) acrylates, acrylate copolymers, polyalkyl alkacrylates wherein the alkyl and alk groups independently contain one to six carbon atoms, polyacrylonitrile, polyvinylacetate, cellulose acetate butyrate, nitrocellulose, copolymers of urethane/carbonate, copolymers of styrene/maleic acid, and mixtures thereof. Copolymers of urethane/carbonate include polycarbonates that are diol terminated which are then reacted with a diisocyanate such as methylene bisphenyl diisocyanate to provide for the urethane/carbonate copolymers. Likewise, copolymers of styrene/maleic acid refer to copolymers having a ratio of styrene to maleic acid of from about 7:3 to about 3:7. Preferably, the biocompatible polymer is also non-inflammatory when employed in situ. The particular biocompatible polymer employed is not critical and is selected relative to the viscosity of the resulting polymer solution, the solubility of the biocompatible polymer in the biocompatible solvent, and the like. Such factors are well within the skill of the art.

The polymers of polyacrylonitrile, polyvinylacetate, poly($C_1$-$C_6$) acrylates, acrylate copolymers, polyalkyl alkacrylates wherein the alkyl and alk groups independently contain one to six carbon atoms, cellulose acetate butyrate, nitrocellulose, copolymers of urethane/carbonate, copolymers of styrene/maleic acid and mixtures thereof typically will have a molecular weight of at least about 50,000 and more preferably from about 75,000 to about 300,000.

Preferred biocompatible polymers include cellulose diacetate and ethylene vinyl alcohol copolymer. In one embodiment, the cellulose diacetate has an acetyl content of from about 31 to about 40 weight percent. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the implanting properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 8 weight-volume percent of the ethylene vinyl alcohol copolymer in DMSO has a viscosity equal to or less than 60 centipoise at 20° C. and more preferably 40 centipoise or less at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution. In a particularly preferred embodiment, the copolymers employed herein comprise a mole percent of ethylene of from about 25 to about 60 and a mole percent of vinyl alcohol of from about 40 to about 75, more preferably a mole percent of ethylene of from about 40 to about 60 and a mole percent of vinyl alcohol of from about 40 to about 60.

The term "contrast agent" refers to a biocompatible (non-toxic) radiopaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. The term "water insoluble contrast agent" refers to contrast agents which are insoluble in water (i.e., has a water solubility of less than 0.01 milligrams per milliliter at 20° C.) and include tantalum, tantalum oxide and barium sulfate, each of which is commercially available in the proper form for in vivo use and preferably having a particle size of 10 μm or less. Other water insoluble contrast agents include gold, tungsten and platinum powders. Methods for preparing such water insoluble biocompatible contrast agents having an average particle size of about 10 μm or less are described below. Preferably, the contrast agent is water insoluble (i.e., has a water solubility of less than 0.01 mg/ml at 20° C.).

The term "encapsulation" as used relative to the contrast agent being encapsulated in the precipitate is not meant to infer any physical entrapment of the contrast agent within the precipitate much as a capsule encapsulates a medicament. Rather, this term is used to mean that an integral coherent precipitate forms which does not separate into individual components, for example into a copolymer component and a contrast agent component.

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, ethyl lactate, acetone, and the like. Aqueous mixtures with the biocompatible solvent can also be employed provided that the amount of water employed is sufficiently small that the dissolved polymer precipitates upon injection into a human body. Preferably, the biocompatible solvent is ethyl lactate or dimethylsulfoxide.

The compositions employed in the methods of this invention are prepared by conventional methods whereby each of the components is added and the resulting composition mixed together until the overall composition is substantially homogeneous. For example, sufficient amounts of the selected polymer are added to the biocompatible solvent to achieve the effective concentration for the complete composition. Preferably, the composition will comprise from about 2.5 to about 8.0 weight percent of the polymer based on the total weight of the composition and more preferably from about 4 to about 5.2 weight percent. If necessary, gentle heating and stirring can be used to effect dissolution of the polymer into the biocompatible solvent, e.g., 12 hours at 50° C.

Sufficient amounts of the contrast agent are then optionally added to the biocompatible solvent to achieve the effective concentration for the complete composition. Preferably, the composition will comprise from about 10 to about 40 weight percent of the contrast agent and more preferably from about 20 to about 40 weight percent and even more preferably about 30 to about 35 weight percent. When the contrast agent is not soluble in the biocompatible solvent, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, gamma irradiation, or electron beam induced polymerization employing, as necessary, a polymerization catalyst or polymerization initiator to provide for the polymer composition. The specific manner of polymerization is not critical and the polymerization techniques employed do not form a part of this invention. In order to maintain solubility in the biocompatible solvent, the polymers described herein are preferably not cross-linked.

In another particularly preferred embodiment of the non-aqueous solution, the biocompatible polymer composition can be replaced with a biocompatible prepolymer composition containing a biocompatible prepolymer. In this embodiment, the composition comprises a biocompatible prepolymer, an optional biocompatible water insoluble contrast agent preferably having an average particle size of about 10 μm or less and, optionally, a biocompatible solvent.

The term "biocompatible prepolymer" refers to materials which polymerize in situ to form a polymer and which, in the amounts employed, are non-toxic, chemically inert, and substantially non-immunogenic when used internally in the patient and which are substantially insoluble in physiologic liquids. Such a composition is introduced into the body as a mixture of reactive chemicals and thereafter forms a biocompatible polymer within the body. Suitable biocompatible prepolymers include, by way of example, cyanoacrylates, hydroxyethyl methacrylate, silicon prepolymers, and the like. The prepolymer can either be a monomer or a reactive oligomer. Preferably, the biocompatible prepolymer is also non-inflammatory when employed in situ.

Prepolymer compositions can be prepared by adding sufficient amounts of the optional contrast agent to the solution (e.g., liquid prepolymer) to achieve the effective concentration for the complete polymer composition. Preferably, the prepolymer composition will comprise from about 10 to about 40 weight percent of the contrast agent and more preferably from about 20 to about 40 weight percent and even more preferably about 30 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 µm or less and more preferably at from about 1 to about 5 µm (e.g., an average size of about 2 µm).

When the prepolymer is liquid (as in the case of polyurethanes), the use of a biocompatible solvent is not absolutely necessary but may be preferred to provide for an appropriate viscosity in the nonaqueous solution. Preferably, when employed, the biocompatible solvent will comprise from about 10 to about 50 weight percent of the biocompatible prepolymer composition based on the total weight of the prepolymer composition. When a biocompatible solvent is employed, the prepolymeric composition typically comprises from about 90 to about 50 weight percent of the prepolymer based on the total weight of the composition.

In a particularly preferred embodiment, the prepolymer is cyanoacrylate which is preferably employed in the absence of a biocompatible solvent. When so employed, the cyanoacrylate adhesive is selected to have a viscosity of from about 5 to about 20 centipoise at 20° C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilized and then stored preferably in sealed amber bottles or vials until needed.

Specific embodiments of nonaqueous solutions suitable for use in the apparatus and methods of the invention are described in U.S. Pat. No. 5,667,767 dated Sep. 16, 1997, U.S. Pat. No. 5,580,568 dated Dec. 3, 1996 and U.S. Pat. No. 5,695,480 dated Dec. 9, 1997 and International Publication Number WO 97/45131 having an International Publication Date of Dec. 4, 1997, the entire contents of which are incorporated herein by this reference.

The first aspect of the method of the invention to treat morbid obesity by forming implants in the human gastrointestinal tract may be described as follows. Let it be assumed that in preparing for the procedure, the gastrointestinal tract of a patient has previously been evaluated by using any or all techniques and procedures available in the art including, but not limited to, upper gastrointestinal radiographic studies, endoscopy with biopsies and gastrointestinal motility studies. Assuming that the patient's pretreatment evaluation diagnoses intractable morbid obesity which warrants the procedure hereinafter described, the patient can be brought into an outpatient clinic or an operating room in a hospital. The patient is preferably placed in a semi-recumbent or lateral decubitus position on an operating or examining table or on a gurney.

After intravenous access has been accomplished and the patient has been appropriately sedated or anesthetized, the distal extremity of probe 42 is introduced through mouth 26 of the patient into stomach 24. In this regard, the handle of probe 42 is grasped by the physician to introduce the distal extremity of probe 42 into mouth 26 and advance it down esophagus 22 to the vicinity of stomach 24 and pylorus 25, the area to be treated. The optical viewing device facilitates advancement by the physician of probe 42.

The distal end portion of needle assembly 43 is introduced through probe 42 and advanced until the distal end portions of needle 44 and sleeve 46 are in the vicinity of the distal extremity of probe 42. Under the guidance of the optical viewing device, the distal extremity of the probe 42 is maneuvered to a position above or intraluminal of the portion of wall 27 which is to be treated. In a preferred method, the distal extremity of probe 42 is positioned in the vicinity of pyloric sphincter 25. The physician retracts sleeve 46 relative to needle 44 so that the distal end portion of needle 44 extends beyond the distal end portion of sleeve 46 a desired amount. The physician primes needle 44 with the saline or other aqueous or physiologic solution.

After the physician penetrates wall 27 with the sharpened end of needle 44, in one of the methods of the invention a saline or other suitable aqueous or physiological solution, referred to herein as the saline solution, can be injected into wall 27 and more specifically into one or both of circular muscle layer 32 and longitudinal muscle layer 33 or between the two muscle layers. The saline injection creates an enlargement in the wall 27 that has an internal space filled with the saline solution. The amount of injected saline solution can range from 0.25 to 10 cc and preferably ranges from 1 to 3 cc.

After creation of the saline-filled enlargement, the physician retracts needle 44 from wall 27, withdraws the remaining saline solution from the needle passage and cleanses the needle passage with DMSO to ensure that the saline solution has been removed from the passage. Removal of the saline solution from the needle passage and the cleansing of the passage with DMSO inhibits premature precipitation within syringe of the biocompatible polymer in the implant forming solution from the DMSO in the implant forming solution. The needle passage is next primed with the implanting forming solution.

The physician causes the distal end portion of needle 44 to penetrate the enlargements and extend into the saline filled space therein. Thereafter, the physician causes a preselected amount of the implant forming solution to be introduced through needle 44. The optional contrast agent within the implanting forming solution permits the viewing of the solution by means of fluoroscopy. In addition, the introduction of the implant forming solution into wall 27 can be monitored by transabdominal or transesophageal ultrasound. The rate of injection of the implant forming solution into the space can range from 0.1 cc per minute to 10 cc per minute.

Figure 2:
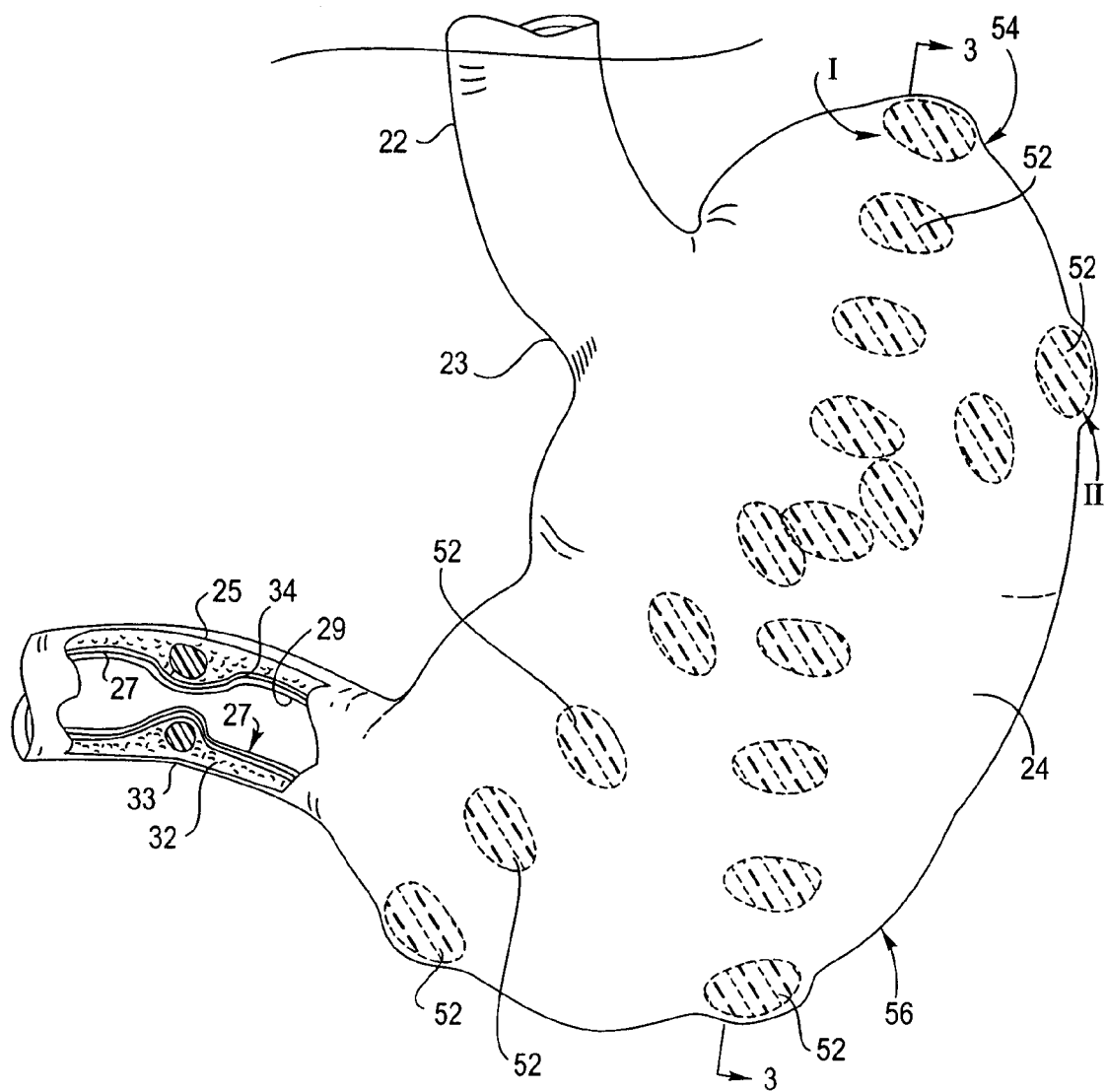
FIG. 2 is a frontal view, partially cut away, of the lower esophagus, stomach and pylorus with implants formed therein in accordance with the method of the present invention.
Figure 3:
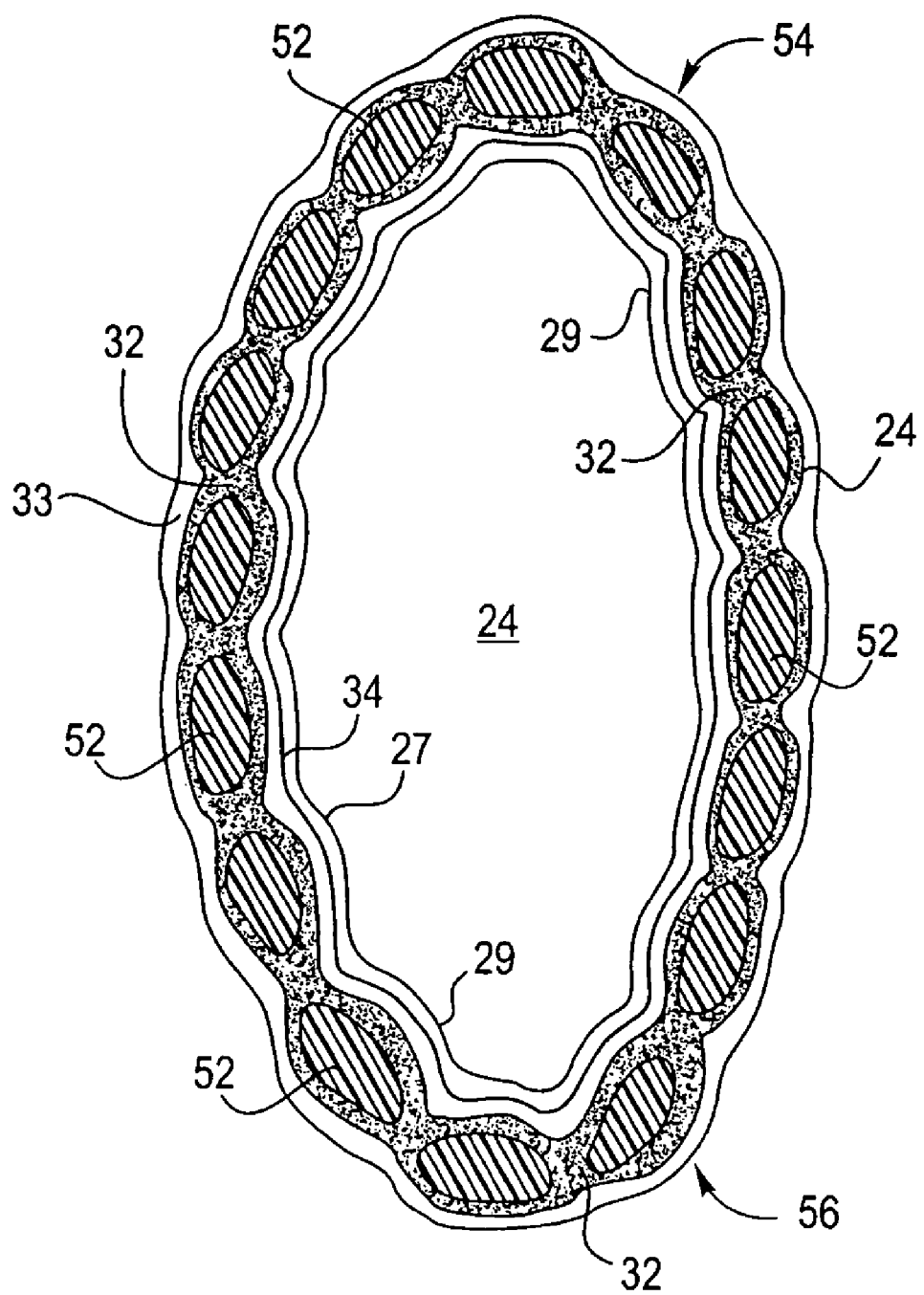
FIG. 3 is a cross-sectional view of the stomach taken along the line 3-3 of FIG. 2.
Figure 4:
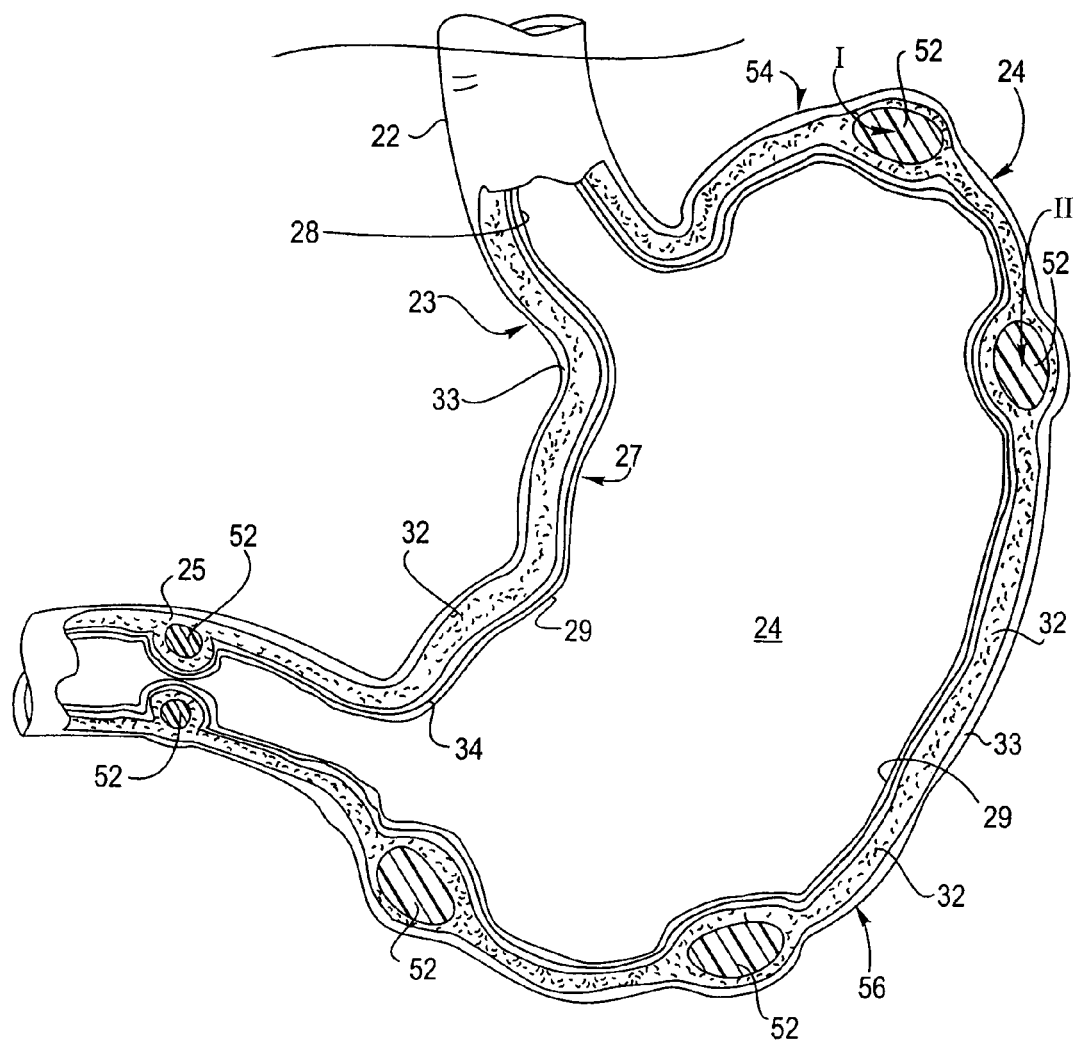
FIG. 4 is a frontal view, similar to FIG. 2 and partially cut away, of the lower esophagus, stomach and pylorus with implants formed therein in accordance with the method of the present invention.

Once the implant forming solution has been introduced into wall 27, the biocompatible polymer of the implant forming solution precipitates to form one or more discrete deposits or solid implants 52 (see FIGS. 2 and 4). The amount of implant forming solution injected into wall 27 for each implant 52 can range from 0.05 cc to 10 cc. The ratio of implant forming solution to saline in the space can range from 2:1 to 1:8 and preferably ranges from approximately one part implant forming solution to two to three parts saline solution. In one embodiment, the space created by the saline solution predefines the configuration of the precipitant or implant 52. The discrete implant 52 can occupy less than all of the space or, alternatively, more implant forming solution than saline can be introduced into wall 27 so that the discrete implant 52 more than fills the space created by the saline.

After completion of the injection of implant forming solution and the solidification of the biocompatible polymer, the remaining solution within the space disperses within body 21 and the space contracts about implant 52.

It has been found that an injection of a suitable aqueous or physiologic solution such as a saline solution into wall 27 prior to the injection of the augmenting solution creates a space (not shown) which is more bulbous than elongate in configuration. The injection of the implant forming solution into such saline filled space facilitates rapid precipitation and enhanced solidification of the biocompatible polymer. This rapid solidification facilitates the desired shaping of implant 52, which is shown in FIG. 2 as being somewhat spherical and elongated in shape. It has also been found that the saline solution facilitates the creation of a relatively soft and spongy implant 52.

The injection of the saline solution into the wall 27 prior to the injection of the implant forming solution serves to condition or prepare the tissue in the wall 27, that is to help the wall 27 receive the implant forming solution and thus facilitate implantation of the biocompatible polymer. In this regard, the saline solution enhances the body's acceptance of the implant forming solution by minimizing the rejection response to the implant 52 and contributing to the body's healing response to the implant. The saline solution also enhances the resolution of any irritative or inflammatory reaction of the body to the DMSO. It should be appreciated that the invention is broad enough to cover any introduction of a solution into the tissue of the body to condition or prepare the tissue for treatment and thereafter performing a treatment on the tissue. Although the conditioning solution has been described as a saline solution, antibiotics and/or anti-inflammatories can be introduced locally to condition the tissue.

The use of a saline solution as discussed above also facilitates the rapid dispersion of the DMSO from the implant forming solution thus diluting any local irritant effect of the DMSO. The saline solution further acts as a heat sink for the heat of dissolution of the solvent.

A plurality of implants 52 are preferentially created in wall 27 in the method of the invention. The number and configuration of implants 52 formed in wall 27 can vary. Specific examples of implant configurations are disclosed in U.S. Pat. No. 6,251,063. In one preferred method of the invention, a plurality of implants 52 are created in wall 27 in the vicinity of pyloric sphincter 25 to create a stenosis in pyloric sphincter 25 and/or a reduction in distensibility in the gastrointestinal wall forming pyloric sphincter 25 by bulking, thickening or tightening the same. The implants 52 are each somewhat pillow-like in shape and are preferably circumferentially spaced-apart or disposed around the periphery of pylorus 25. More specifically, implants 52 are disposed substantially in a plane extending perpendicularly to a longitudinal axis extending along the centerline of pylorus 25. An exemplary rosette of four implants 52 spaced-apart around the center of the rosette at approximately 90° intervals is partially shown in FIGS. 2 and 4. It should be appreciated, however, that less than four or greater than four implants 52 can be provided and formed in wall 27 and can be circumferentially spaced-apart at approximately equal angular intervals or asymmetrically disposed about the center line of pylorus 25. A plane of implants can be disposed above, below and/or at pylorus 25. As indicated, in other configurations, implants can be formed which are not disposed in a single plane. A plurality of implants may also be formed in additional planes spaced apart from a first plane of implants. Such an array of implants can be longitudinally centered on pylorus 25. In another configuration, a single implant can be provided for augmenting or partially or completely coapting pylorus 25. Implants 52 which merge with adjacent implants 52 in wall 27 are within the scope of the present invention.

The implantable material can be injected into any layer of the wall, such as mucosa 29 or submucosa 34, although it is preferred that the implantable material be deposited into one or both of circular and longitudinal muscles 32 and 33 in the wall. The shape of the implants can vary. In this regard, the implants can be discrete depositions that are circular or ball-like or that have any other shape. Alternatively, the implants can be depositions with finger-like or lake-like extensions or, as disclosed in U.S. Pat. No. 6,251,064, the entire content of which is incorporated herein by this reference, extend arcuately around at least a portion of pylorus 25 and possibly completely around pylorus 25 in a ring-shaped or ring-like manner.

The procedure of the first aspect of the invention serves to increase gastric emptying times and thus prolong periods of satiety. Although implants 52 do not make a non-functioning pyloric sphincter, they do create some level of stenosis to delay gastric emptying and thus cause longer periods of gastric distention. Gastric fullness causes longer periods of satiety and reduction of the appetite.

The optional contrast agent in the implants permits the implants to be monitored after completion of the procedure described above. Thus the stability of the implant and its configuration can be observed over time. Further procedures can be performed to supplement previously formed implants. It should be appreciated that the implants of the present invention can be used as delivery vehicles for other materials such as radio-isotopes, chemotherapeutic agents, anti-inflammatory agents and/or antibiotics.

Although the method of the invention has been described as including the formation of a space by a saline solution injected into the wall 27 prior to an injection of implant forming solution into the wall 27, it should be appreciated that such space can be formed by other aqueous or physiologic solutions or by a local anesthetic. Alternatively, the implant forming solution can be injected into wall 27 without the prior formation of such a space by an injection of saline solution or otherwise. The implant forming solution can also be injected directly into the wall 27 without an injection of saline or any other solution for any secondary purpose described herein or otherwise. A saline or other aqueous or physiologic solution can optionally be introduced into such a space formed by the implant forming solution, that is after the introduction of the implant forming solution into the wall 27, to facilitate dispersion of the DMSO or other biocompatible solvent present in the implant forming solution. It can thus be seen that the invention is broad enough to cover the introduction of any conditioning solution into the tissue after the treatment to facilitate the treatment.

In a second aspect of the method of the present invention, which can be performed separately or in combination with the first aspect of the invention, one or more implants are made in the wall of the stomach to decrease the distensibility and contractility of the muscle of the stomach. The implants can be formed by any of the methods discussed above and can be any of the shapes discussed above. If more than one implant is made, any of the configurations of implants disclosed above can be utilized.

In one preferred method of treatment, one or more implants 52 are made in wall 27 of stomach 24 that extend across one or more portions of stomach 24. For example, spaced-apart injections can be made in the portions of stomach 24 as shown in FIG. 2. Alternatively, or in addition to such spaced-apart implants 52, an elongate or band-like implant can be formed, for example in accordance with the method disclosed in U.S. Pat. No. 6,251,064. An exemplary implant configuration 53 shown in FIGS. 2 and 4 extends from the top to the bottom of the stomach, that is in a vertical, circular or semi-circular fashion, from the upper part or fundus 54 of stomach 24 down towards the lower part or antrum 55 of stomach 24. An alternate exemplary implant configuration 56, also shown in FIGS. 2 and 4, extends diagonally from a two o'clock position to an eight o'clock position across a portion of stomach 24.

The injections can thus be in a sequential fashion and can each range from 0.25 to 20.0 cubic centimeters and preferably range from 0.5 to 3.0 cubic centimeters of implantable material per injection. The injections can either be in one portion of the stomach, such as one half or one side of the stomach, or in a complete semi-circular or spherical fashion around the front portion, the underneath portion, the back portion and/or the top portion of the stomach. Of course, the one or more implants can extend along any irregularly-shaped path along any portion of the wall of the stomach. In addition to or as an alternative to the foregoing, one can make random implantations in a sufficient number of places in the stomach to reduce or stop free propulsive or effective movement of the stomach from the back of the stomach towards the pylorus.

The decrease in the distensibility and contractility of the muscle of stomach 24 resulting from implants 52 formed from the second aspect of the invention provoke longer gastric emptying times and thereby prolong periods of sensation of fullness and satiety, yet at the same time allow food to pass in a very slow fashion. Such one or more implants 52 thereby act in a substantially mechanical manner to alter stomach peristalsis and motility so as to prolong the transit time of materials in and/or through stomach 24. In so doing, however, reflux pressure on lower esophageal sphincter 23, which is already strained in obese patients, can be increased.

The first and second aspects of the invention can also use other techniques for prolonging satiety. One group of such techniques involves partitioning stomach 24 to reduce its volume. Sutures, staples and glues can be so used to wall off portions of stomach 24. For example, sutures, staples and/or glues can be placed across any portion of stomach 24, such as along the configurations hereinbefore described, so as to reduce the volume of the stomach. Other such techniques can utilize rings, bands or other mechanical devices placed around lower esophageal sphincter 23 for creating a mechanical valve to reduce reflux through sphincter 23. Rings, bands and other mechanical devices can also be placed around the cardia to create a mechanical valve that limits expansion of the stomach and thus prolongs satiety.

Figure 5:
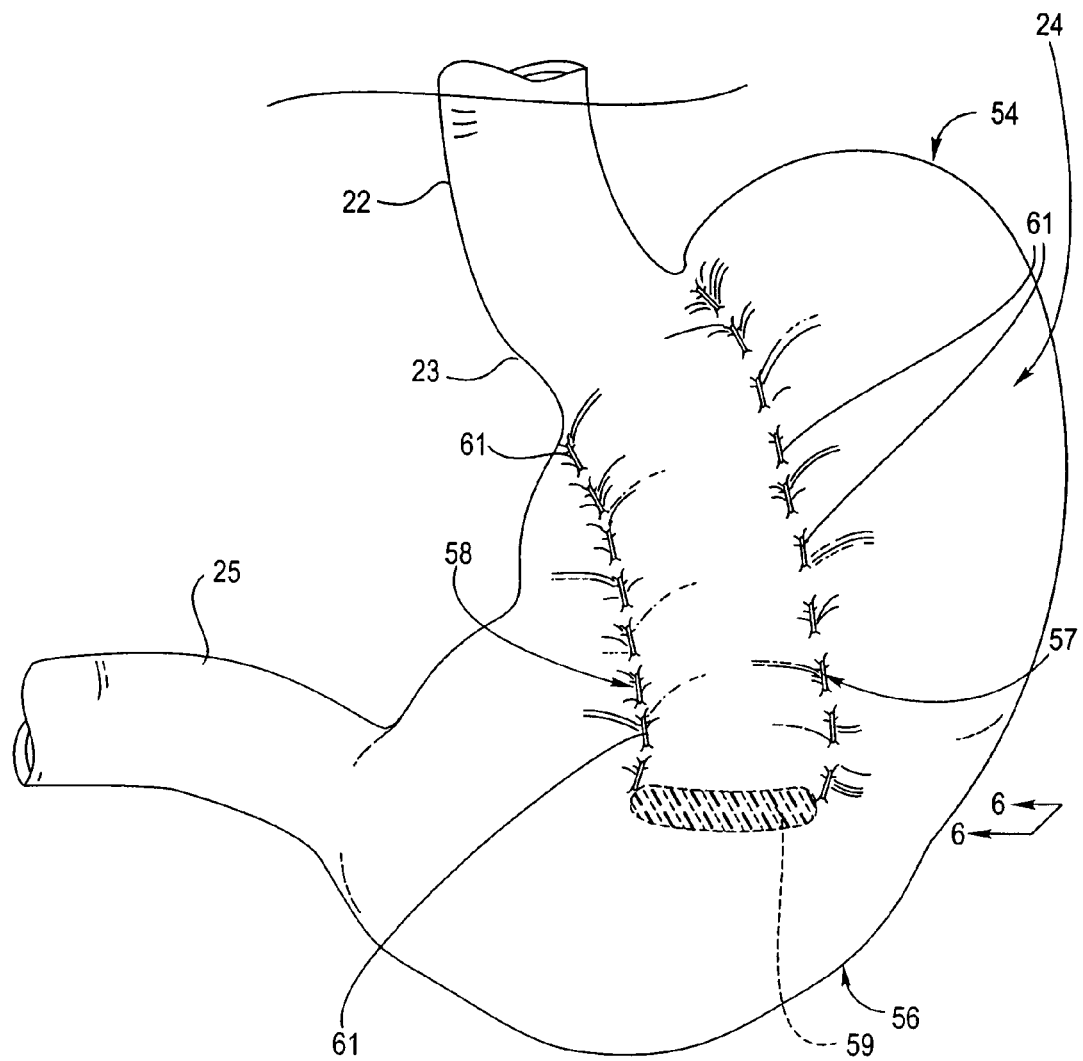
FIG. 5 is a frontal view of the lower esophagus, stomach and pyloric region treated by an alternative method of the present invention.
Figure 6:
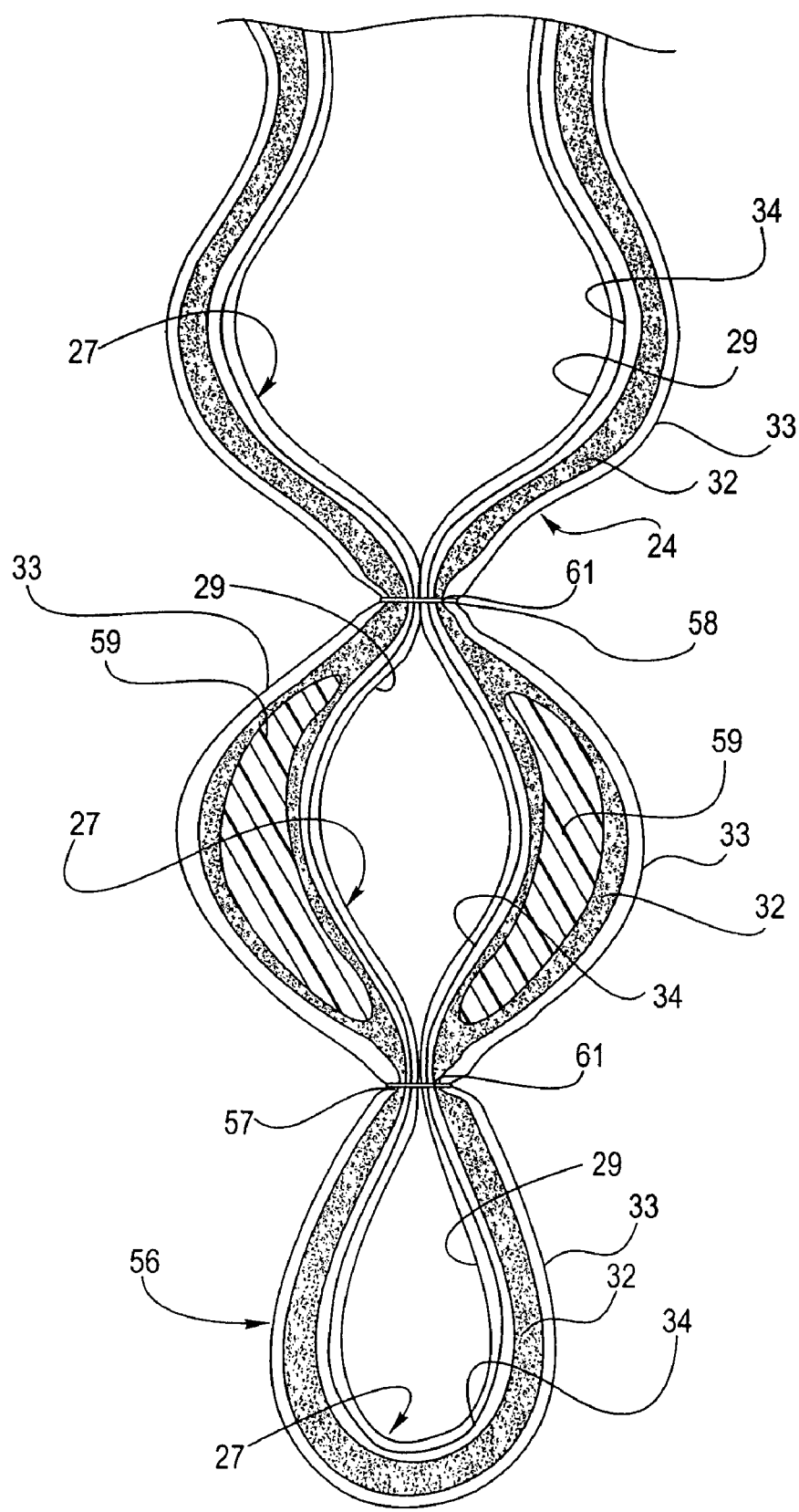
FIG. 6 is a cross-sectional view of the pyloric region and stomach taken along the line 6-6 of FIG. 5.

In a third aspect of the invention, an artificial sphincter can be formed in the wall 27 of the stomach for assisting the lower esophageal sphincter. In one preferred method of the invention, first and second spaced-apart walls 57 and 58 are formed in stomach 24 to create a tubular extension extending through a portion of the stomach 24 (see FIG. 5). First and second walls 57 and 58 can be formed from any technique, such as those discussed above for partitioning stomach 24. Such techniques include sutures, staples and glues. In a preferred embodiment of the third aspect of the invention, first and second artificial walls 57 and 58 each commence in the vicinity of the entrance of the stomach 24, on opposite sides of the terminus of the esophagus 22, and terminate at an artificial sphincter 59 created in wall 27 of stomach 24 by any of the techniques and by using any of the implantable materials, in each case, as hereinbefore described. In one exemplary procedure, walls 57 and 58 are created by securing together opposite sides of the stomach wall 27 with titanium gastrointestinal staples 61, or any appropriate alloy staples known in the art, as shown in FIG. 5. In this manner, ingested matter is prevented from being propelled distally, towards the pylorus, without first having to traverse artificial sphincter 59. One or more implants 60 creating new sphincter 59, which serves as a secondary antireflux barrier, are preferably formed in muscle layer 32 of wall 27 so as to reduce the distensibility of wall 27 and thus form and provide a sphincter mechanism which, in turn, inhibits reflux. The implants 60 are preferably similar to implants 52 and formed by any of the methods discussed above. Any suitable configuration of implants 60, such as a plurality of circumferentially spaced-apart implants or one or more ring or arcuate-shaped implants, formed in one and preferably in both of the opposite stomach walls 27 can be used for forming the secondary sphincter. Implants 60 are shown in FIGS. 5 and 6 as being arcuate-shaped implants. Together, walls 57 and 58 and secondary sphincter 59 create an additional barrier which aids LES 23 in inhibiting reflux.

In an alternative embodiment of the third aspect of the present invention a portion of stomach 24 is excluded or isolated by one of walls 57 and 58. In one exemplary embodiment, first wall 57 preferably is formed to extend beyond secondary sphincter 59 to the greater curvature of stomach 24 in order to fully partition stomach 24 and thereby exclude a portion thereof from use and thus prolong satiety. Such extended portion of first wall 57 is shown in phantom lines in FIG. 5 and labeled as extended wall 57' therein.

Each of the aspects of the invention discussed above can be supplemented by the formation of one or more implants in the wall 27 of the gastrointestinal tract in the vicinity of the lower esophageal sphincter 23 to enhance the reflux barrier created by the lower esophageal sphincter. Such implants can be formed in the manner discussed above from any suitable implant forming solution. Exemplary procedures and apparatus for forming implants in the vicinity of lower esophageal sphincter 23 are disclosed in U.S. Pat. Nos. 6,251,063 and 6,251,064.

Figure 7:
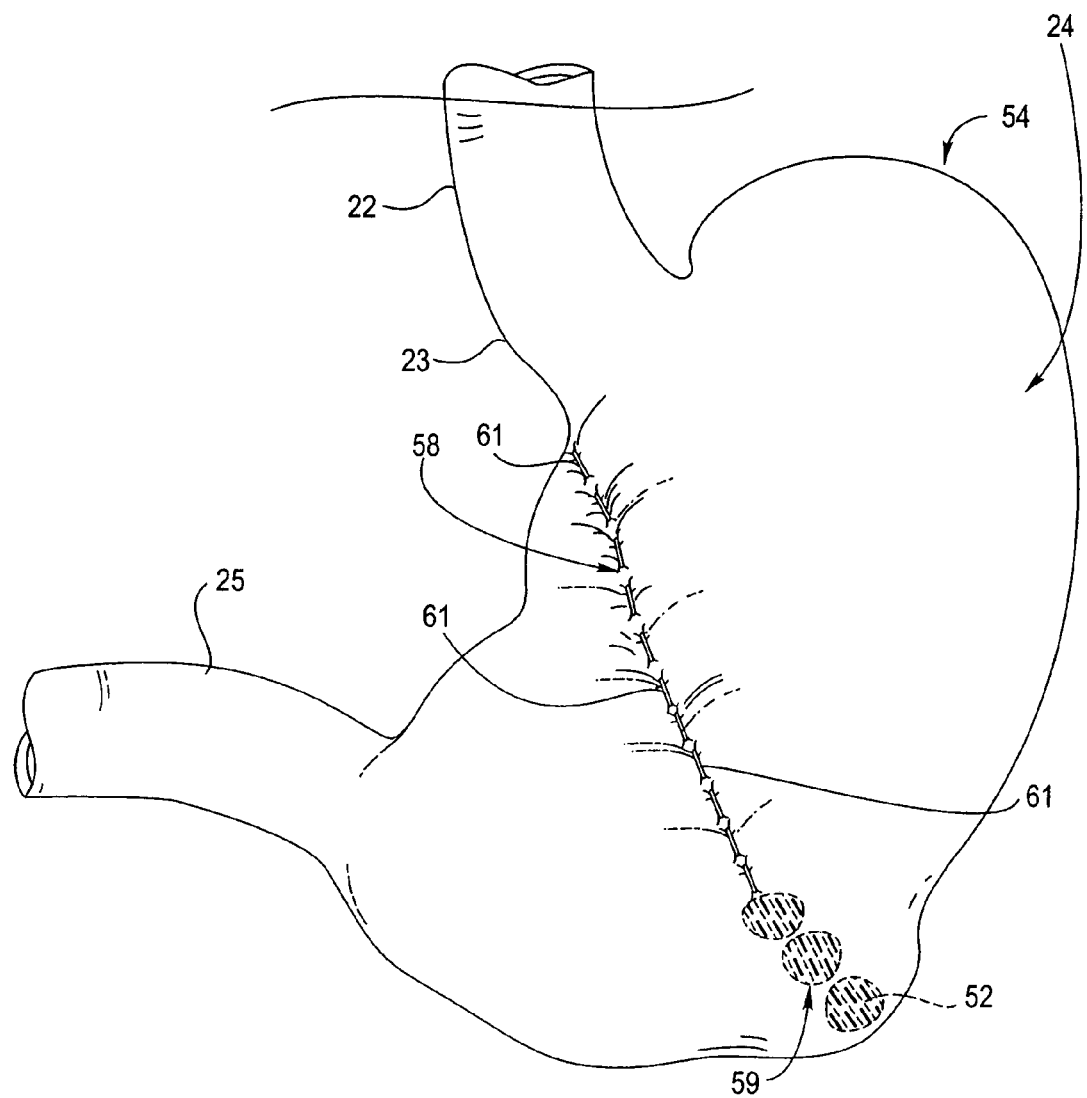
FIG. 7 is a frontal view of the lower esophagus, stomach and pyloric region treated by an alternative method of the present invention.

In a fourth aspect of the invention, stomach 24 is provided with a single wall 71, which is similar to first wall 57 but extends from the upper portion of the stomach 24 adjacent the terminus of the esophagus 22 to the greater curvature of stomach 24 so as to fully partition stomach 24 (see FIG. 7). Wall 71 can be formed from any of the techniques discussed above, such as sutures, staples or glues, and as shown is formed by staples 61 which secure together opposite sides of the stomach wall 27 along the length of the artificial wall 71. At least one and as shown a plurality of implants 72 are formed in esophageal wall 27 in the vicinity of lower esophageal sphincter 23 for inhibiting reflux from stomach 24 into the esophagus 22. The implants 72 can be formed in any of the manners discussed above from any suitable implant forming material, such as any of the implant forming materials discussed above and preferably any of the implant forming solutions discussed above, and can have any of the shapes discussed above. Although the implants 71 can be formed in any layer of wall 27, the implants are preferably formed in one or both of circular muscle layer 32 and longitudinal muscle layer 33 or between the two muscle layers. Where a plurality of implants 71 are formed in wall 28, any suitable configuration of implants can be used.

In conjunction with the fourth aspect of the invention, implants can optionally be formed in wall 27 in the vicinity of the pylorus 25, as discussed above in the first aspect of the invention, and/or in wall 27 in stomach 24, as discussed above in the second aspect of the invention. As more fully set forth above, the formation of implants 52 in the vicinity of pylorus 25 and/or in wall 27 of stomach 24 prolong periods of satiety by reducing gastric emptying times.

As discussed above, the implants formed by the various aspects of the invention serve to alter the wall in which they are formed in a mechanical manner, that is by their presence in the wall. The implants also act in a nonmechanical manner to alter the characteristics of the wall by modifying sensory motor nervous feedback and control in the wall. It should be appreciated that such a modification of sensory motor nervous feedback and control can be accomplished by the implants alone or in conjunction with an application of energy to such portion of the body wall. Suitable sources for such energy include radio frequency, laser and microwave energy applied to the wall in a conventional manner, such as by means of a probe or stylet disposed adjacent to the wall or introduced into the wall.

It should be appreciated that the approach and the access to pylorus 25 and stomach 24 for the methods of the present invention can be endoscopic, laparoscopic or by open surgery. The introduction of the implantable material can be transmucosal, from the inside towards the out, or transserosal, from the outside in. In any event, the injections are preferably directed into the muscle of the stomach The numerical sizes and ranges in the foregoing drawings are merely exemplary and not intended to be limiting of the purview of the invention.

From the foregoing, it should be appreciated that an improved method of treating morbid obesity has been described. The method includes forming and placing implants in the walls of the stomach and/or pylorus to effectively create barriers to gastric peristalsis and the forward propulsion of stomach contents and/or to alter the motility of the stomach contents through the modification of sensory motor nervous feedback and control. The method is relatively non-invasive and serves to prolong satiety. Limiting gastric distensibility and prolonging gastric emptying times in this manner, while optionally enhancing the lower esophageal sphincter to inhibit gastroesophageal reflux, provides a novel, effective and safe method for treating a dangerous, yet common, condition.

The foregoing and other aspects of the invention are set forth in the following claims.

What is claimed is:

1. A method for treating morbid obesity in a body of a mammal having a gastrointestinal tract extending through a stomach and a pyloric sphincter formed by a wall having a muscle layer comprising the step of forming at least one implant in the muscle layer of the wall to inhibit emptying of the stomach.

2. The method claim 1 wherein the forming step includes the step of forming a plurality of implants in the wall in the vicinity of the pyloric sphincter.

3. The method of claim 2 wherein the forming step includes the step of forming a plurality of circumferentially-disposed implants in the wall in the vicinity of the pyloric sphincter.

4. The method of claim 1 wherein the implant is arcuate shaped.

5. The method of claim 1 further comprising the step of inhibiting the ability of the stomach to expand so as to prolong satiety.

6. The method of claim 5 wherein the inhibiting step includes the step of forming a wall across a portion of the stomach to exclude a portion of the stomach from use.

7. The method of claim 1 wherein the forming step includes injecting a biocompatible solution having a biocompatible polymer and a biocompatible solvent into the wall.

8. The method of claim 7 wherein the biocompatible solution includes a contrast agent.

9. The method of claim 7 wherein the biocompatible solution of the biocompatible polymer and the biocompatible solvent has a composition comprising from about 2.5 to about 8.0 weight percent of a biocompatible polymer, from about 10 to about 40 weight percent of a water insoluble biocompatible contrast agent and from about 52 to about 87.5 weight percent of a biocompatible solvent.

10. A method for treating morbid obesity in a body of a mammal having a gastrointestinal tract extending though a stomach formed by a wall comprising the step of introducing a biocompatible solution into the wall to form at least one implant in the wall of the stomach to provoke longer periods of satiety.

11. The method of claim 10 wherein the forming step includes the step of forming a plurality of implants in the wall of the stomach.

12. The method of claim 11 wherein the plurality of implants extend across a portion of the stomach.

13. The method of claim 11 wherein the plurality of implants extend around the stomach.

14. The method of claim 10 wherein the wall has a muscle layer, the at least one implant being formed in the muscle layer of the wall.

15. The method of claim 10 wherein the forming step includes the step of forming at least one implant in the wall of the stomach to decrease the contractility of the wall.

16. The method of claim 10 wherein the forming step includes the step of forming at least one implant in the wall of the stomach to modify the sensory motor nervous feedback and control in the wall.

17. The method of claim 10 wherein the biocompatible solution includes a biocompatible polymer and a biocompatible solvent.

18. The method of claim 17 wherein the biocompatible solution includes a contrast agent.

19. The method of claim 17 wherein the biocompatible solution of the biocompatible polymer and the biocompatible solvent has a composition comprising from about 2.5 to about 8.0 weight percent of a biocompatible polymer, from about 10 to about 40 weight percent of a water insoluble biocompatible contrast agent and from about 52 to about 87.5 weight percent of a biocompatible solvent.

* * * * *